United States Patent
Shaik et al.

(10) Patent No.: US 9,598,329 B2
(45) Date of Patent: Mar. 21, 2017

(54) ETHYLENE OLIGOMERIZATION PROCESS

(71) Applicant: Saudi Arabian Oil Company, Dhahran (SA)

(72) Inventors: Kareemuddin Mahaboob Shaik, Dhahran (SA); Wei Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 318 days.

(21) Appl. No.: 13/891,607

(22) Filed: May 10, 2013

(65) Prior Publication Data

US 2013/0303817 A1    Nov. 14, 2013

Related U.S. Application Data

(60) Provisional application No. 61/645,704, filed on May 11, 2012.

(51) Int. Cl.
*C07C 2/08*    (2006.01)
*C07C 2/30*    (2006.01)
*B01J 19/24*   (2006.01)

(52) U.S. Cl.
CPC ............... *C07C 2/08* (2013.01); *B01J 19/241* (2013.01); *B01J 19/2415* (2013.01); *C07C 2/30* (2013.01); *B01J 2219/00006* (2013.01); *B01J 2219/00094* (2013.01); *B01J 2219/00108* (2013.01); *B01J 2219/00777* (2013.01)

(58) Field of Classification Search
CPC .... C07C 2/08; C07C 2/30; B01J 2219/00777; B01J 2219/00108; B01J 2219/00006; B01J 2219/00094; B01J 19/241; B01J 19/2415; B01J 19/006; B01J 19/2405

USPC .......................... 585/504; 422/187, 135, 228
See application file for complete search history.

(56) References Cited

U.S. PATENT DOCUMENTS 2,614,132 A * 10/1952 Lee et al. ...................... 585/310
2,908,556 A    10/1959 Watson et al.
3,686,350 A     8/1972 Yamada et al.
3,879,485 A     4/1975 Belov et al.
(Continued)

FOREIGN PATENT DOCUMENTS

AU    611473 B2    6/1991
EP    0200654 B1    6/1988

OTHER PUBLICATIONS

Jam Petrochemical Company, "Project Definition Butene 1", pp. 1-15, www.jpcomplex.com/pps/B-1%20PRESENTATION.pps.
(Continued)

*Primary Examiner* — In Suk Bullock
*Assistant Examiner* — Aaron Pierpont
(74) *Attorney, Agent, or Firm* — Bracewell LLP; Constance G. Rhebergen; Kevin R. Tamm (57) ABSTRACT

An ethylene oligomerization system is useful for creating 1-butene from ethylene in the presence of an ethylene oligomerization catalyst. The ethylene oligomerization system includes an internal baffle single pass reactor, a separation system and an exterior motion driver. The exterior motion driver is operable to induce unsteadiness in the flow of the process fluid contained in the internal baffle single pass reactor by transferring motion into the process fluid. An ethylene oligomerization process is useful for creating a refined 1-butene product from ethylene using the ethylene oligomerization system.

14 Claims, 1 Drawing Sheet

(56) References Cited

U.S. PATENT DOCUMENTS

| | | | |
|---|---|---|---|
| 4,101,600 A | 7/1978 | Zhukov et al. | |
| 4,242,531 A | 12/1980 | Carter | |
| 4,309,387 A | 1/1982 | Carter | |
| 4,528,415 A | 7/1985 | Knudsen | |
| 4,532,370 A | 7/1985 | Le Quan et al. | |
| 4,615,998 A | 10/1986 | Le Quan et al. | |
| 5,030,790 A | 7/1991 | Sergienko et al. | |
| 5,227,562 A | 7/1993 | Wu | |
| 5,260,499 A | 11/1993 | Wu | |
| 5,414,178 A | 5/1995 | Wu | |
| 5,728,912 A | 3/1998 | Saqualain Haider Rizvi et al. | |
| 5,792,895 A | 8/1998 | Commereuc et al. | |
| 5,877,376 A | 3/1999 | Commereuc et al. | |
| 6,334,985 B1 * | 1/2002 | Raghuram et al. | 422/224 |
| 6,429,268 B1 * | 8/2002 | Xiongwei | B01J 19/0013 422/130 |
| 2007/0185362 A1 * | 8/2007 | Lattner | C07C 2/32 585/521 |
| 2009/0245015 A1 | 10/2009 | Ni et al. | |
| 2010/0124145 A1 | 5/2010 | Ni et al. | |
| 2010/0216631 A1 | 8/2010 | Ni et al. | |
| 2011/0288308 A1 | 11/2011 | Grasset et al. | |

OTHER PUBLICATIONS

Xiong-Wei Ni, "Continuous Oscillatory Baffled Reactor Technology", Innovations in Pharmaceutical Technology, Aug. 31, 2006, pp. 90-96, www.iptonline.com/articles/public/page9091939496loresnonprint.pdf.

Forestiere et al., "Oligomerization of Monoolefins by Homogeneous Catalysts", Oil and Gas Science and Technology, 2009, pp. 649-667, vol. 64, No. 6, Institut francais du Petrole.

Simon L. Desset, New Strategies for the Rhodium-Catalysed Aqueous-Biphasic Hydroformylation of Medium Chain Alkenes, A Thesis Submitted for the Degree of PHD at the University of St. Andrews, Jun. 15, 2009, pp. 1-185.

PCT Int'l Search Report and the Written Opinion dated Aug. 6, 2013; Int'l Application No. PCT/US2013/040473; Int'l Filing Date: May 10, 2013.

* cited by examiner

ETHYLENE OLIGOMERIZATION PROCESS

CROSS-REFERENCE TO RELATED PATENT APPLICATIONS

This application claims priority from U.S. Provisional Application No. 61/645,704, filed May 11, 2012. For purposes of United States patent practice, this application incorporates the contents of the Provisional Application by reference in its entirety.

BACKGROUND OF THE INVENTION

1. Field of the Invention

The field of invention relates to the production of alpha-olefins. More specifically, the field relates to the production of alpha-olefins, especially 1-butene, via oligomerization of ethylene.

2. Description of the Related Art

1-Butene is an important petrochemical, especially for the productions of polyethylene. The reaction of ethylene and other alpha-olefins, especially 1-butene, forms various grades of linear low density polyethylene (LLDPE), a useful commercial polymer.

A source of 1-butene is the butene fraction from the effluent of a fluidized catalytic cracker. The process for recovering 1-butene from the effluent of a FCC requires several difficult process steps that make the process undesirable.

Several commercial processes dimerize ethylene into 1-butene. A commercially successful dimerization process is the Alphabutol™ Process, developed by the Intitute Francais du Petrole (IFP), described in A. Forestiere, et al., "Oligomerization of Monoolefins by Homogenous Catalysts", Oil & Science and Technology—Review de l'Institute Francais du Petrole, pgs. 663-664 (Vol. 64, No. 6, November 2009). The process appears to use a loop reactor that contains 1-butene as a process fluid to oligomerize ethylene into 1-butene and other higher-carbon count alpha-olefins.

There is one known problem with loop dimerization systems: polymer and oligomer fouling. Long residence times and poor heat removal from the highly exothermic reactions lead to the formation of polyethylene-based residues. Even with a highly selective oligomerization catalyst, free radical initiators from feed impurities and catalytically active debris (for example, rust) can initiate polymerization of ethylene and other alpha-olefins.

A side effect of chronic fouling is increasingly frequent process shutdowns and higher maintenance costs for removing adhered polymer residues. Polymer builds layer upon layer and eventually closes off openings and ports in locations with low fluid flow rates. A polymer coating along the wall of the reactor acts as an insulator, which negatively affects heat transfer. Polymer can also collect debris that can be catalytically active or that can poison the reaction process.

An especially troublesome issue is the formation of "hot spots". A hot spot is an area where external cooling is ineffective and catalyst activity is high. It represents a loss of process control. A hot spot can be an area of collected polymer that includes catalytically active material that fosters side-reactions, including polymerization. If left unchecked, the hot spot can eventually lead to a process shutdown due to the loss of cooling capacity or a runaway polymerization reaction.

A catalyst inhibitor can halt the undesirable oligomerization and polymerization reaction in the loop reactor effluent. Applying a catalyst inhibitor inside a loop reactor, however, interferes with the desirable oligomerization reaction as it re-circulates back towards the catalyst introduction area. Adding too much inhibitor or allowing it to build up slowly in the recycle loop can kill the oligomerization reaction completely.

To avoid polymer fouling issues, operators of loop-style reactors operate at reduced temperatures or production rates versus optimal production levels or process conditions. Yet, at lower production rates, polymers can build up in stagnant zones of the loop reaction system. Ineffective mixing at lower temperatures and production rates leads to wasted reactants and higher inefficiency. Poor fluid heat transfer at lower production rates can exacerbate the operational problems the operator is attempting to avoid. Lower operating temperature can result in a reduced effective operating window, which makes overall operational control more difficult.

SUMMARY OF THE INVENTION

An ethylene oligomerization system is useful for creating 1-butene from ethylene in the presence of an ethylene oligomerization catalyst. The ethylene oligomerization system includes an internal baffle single pass reactor, a separation system and an exterior motion driver. The internal baffle single pass reactor has an interior wall, an operable length, a proximal end, a distal end, an interior fluid conduit, a set of internal baffles, a process fluid flow pathway, an oligomerization reaction zone that is operable to support an ethylene oligomerization reaction in a process fluid and a catalyst deactivation zone that is operable to support an oligomerization catalyst deactivation reaction in a process fluid. The catalyst deactivation zone is positioned downstream of the oligomerization reaction zone. The internal fluid conduit contains the process fluid and the set of internal baffles. The interior wall and the set of internal baffles define the process fluid flow pathway. The separation system fluidly couples to the distal end of the internal baffle single pass reactor. The separation system is operable to selectively separate separately deactivated oligomerization catalyst, ethylene and 1-butene from a crude product and to produce a refined 1-butene product. The exterior motion driver couples to the internal baffle single pass reactor. The exterior motion driver is operable to induce unsteadiness in the flow of the process fluid contained in the internal baffle single pass reactor by transferring motion into the process fluid.

An embodiment of the ethylene oligomerization system is further operable to selectively separate 1-hexene from the crude product and to produce a refined 1-hexene product. An embodiment of the ethylene oligomerization system is further operable to selectively separate 1-octene from the crude product and to produce a refined 1-octene product. An embodiment of the ethylene oligomerization system is further operable to selectively separate 1-decene from the crude product and to produce a refined 1-decene product.

An ethylene oligomerization process is useful for creating a refined 1-butene product from ethylene using the ethylene oligomerization system. The ethylene oligomerization process includes the step of introducing a reaction solution into the process fluid contained in the internal fluid conduit of the internal baffle single pass reactor at about the proximal end of the reactor such that the process fluid traverses the operative length of the reactor by flowing along the process fluid flow pathway. The ethylene oligomerization process includes the steps of introducing ethylene, an oligomerization pre-catalyst and a co-catalyst separately into the process fluid proximate to the oligomerization reaction zone such that the ethylene, the oligomerization pre-catalyst and the co-catalyst are distributed in the process fluid. The ethylene oligomerization process includes the step of introducing a catalyst inhibitor into the process fluid proximate to the catalyst deactivation zone such that the catalyst inhibitor is distributed in the process fluid. The ethylene oligomerization process includes the steps of operating the ethylene oligomerization system such that an oligomerization catalyst forms in the process fluid from the reaction of the oligomerization pre-catalyst and the co-catalyst in the oligomerization reaction zone, 1-butene forms in the process fluid from the oligomerization reaction of ethylene in the presence of the oligomerization catalyst in the oligomerization reaction zone, a deactivated oligomerization catalyst forms in the process fluid from the reaction of the oligomerization catalyst and the catalyst inhibitor in the catalyst deactivation zone, an external motion driver induces unsteadiness in the flow of the process fluid, a crude product passes into a separation system, the crude product comprising 1-butene, ethylene and the deactivated oligomerization catalyst, and the separation system selectively separates separately the deactivated oligomerization catalyst, the ethylene and the 1-butene from the crude product such that a refined 1-butene product is produced.

The ethylene oligomerization system includes an internal baffle single pass reactor to remedy the problems of poor heat exchange, polymer and heavy oligomer fouling and insufficient mixing of reactants and catalysts. The internal baffle single pass reactor reduces variations in residence time for both the reactants and the products. Reduced variations in operating conditions prevent undesired oligomerization reactions and polymer buildup while maximizing desirable mixing and products. The internal baffles prevent the formation of low flow areas in the single pass reactor.

Configurations of the ethylene oligomerization system support the introduction of oligomerization catalyst inhibitors into the internal baffle single pass reactor while the reactants are in the internal baffle single pass reactor. The application of catalyst inhibitor terminates all oligomerization and side-reactions, and ensures the desired level of ethylene conversion and selection. Any unused catalyst inhibitor passes from the distal end of the internal baffle single pass reactor and does not build up in the reaction system.

The ethylene oligomerization system can be controlled with relative ease compared to a loop reactor system. The internal baffle single pass reactor has more than one reaction zone for introducing reactants and for manipulating the internal operating conditions. The introduction of oligomerization catalyst and catalyst inhibitors into separate reaction zones along the operating length of the internal baffle single pass reactor separately promotes and suppresses reactions to optimize the oligomerization reactions while preventing excessive oligomerization and polymerization.

Inducing unsteadiness into the process fluid as it flows through the internal baffle single pass reactor facilitates reactions and operations management. The unsteady process fluid motion in conjunction with the tortuous internal fluid flow pathway enhances mixing of the reactants and catalyst, which allows for timely termination of the reaction upon application of the inhibitor. The unsteadiness also helps to reduce the formation of oligomers and polymers, improves heat transfer and increases system reliability over analogous loop reactor and single-pass reactor systems. The motion introduced through motion driving means can be oscillatory or asynchronous.

BRIEF DESCRIPTION OF THE DRAWINGS

These and other features, aspects, and advantages of the present invention are better understood with regard to the following Detailed Description of the Preferred Embodiments, appended Claims, and accompanying Figures

DETAILED DESCRIPTION OF THE PREFERRED EMBODIMENTS

The Specification, which includes the Summary of Invention, Brief Description of the Drawings and the Detailed Description of the Preferred Embodiments, and the appended Claims refer to particular features (including process or method steps) of the invention. Those of skill in the art understand that the invention includes all possible combinations and uses of particular features described in the Specification. Those of skill in the art understand that the invention is not limited to or by the description of embodiments given in the Specification. The inventive subject matter is not restricted except only in the spirit of the Specification and appended Claims.

Those of skill in the art also understand that the terminology used for describing particular embodiments does not limit the scope or breadth of the invention. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a", "an" and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "couple" and its conjugated forms means to complete any type of required junction, including electrical, mechanical or fluid, to form a singular object from two or more previously non-joined objects. If a first device couples to a second device, the connection can occur either directly or through a common connector. "Optionally" and its various forms means that the subsequently described event or circumstance may or may not occur. The description includes instances where the event or circumstance occurs and instances where it does not occur. "Operable" and its various forms means fit for its proper functioning and able to be used for its intended use.

Spatial terms describe the relative position of an object or a group of objects relative to another object or group of objects. The spatial relationships apply along vertical and horizontal axes. Orientation and relational words including "upstream" and "downstream" and other like terms are for descriptive convenience and are not limiting unless otherwise indicated.

Where the Specification or the appended Claims provide a range of values, it is understood that the interval encompasses each intervening value between the upper limit and the lower limit as well as the upper limit and the lower limit. The invention encompasses and bounds smaller ranges of the interval subject to any specific exclusion provided. "Substantially free" means less than 1% by the indicated unit of measure.

Where reference is made in the Specification and appended Claims to a method comprising two or more defined steps, the defined steps can be carried out in any order or simultaneously except where the context excludes that possibility.

The disclosure of a patent or publication in this application acts to incorporate the reference in its entirety to more fully describe the state of the art in which the invention pertains except where the reference contradicts a statement made in the application.

Figure 1:
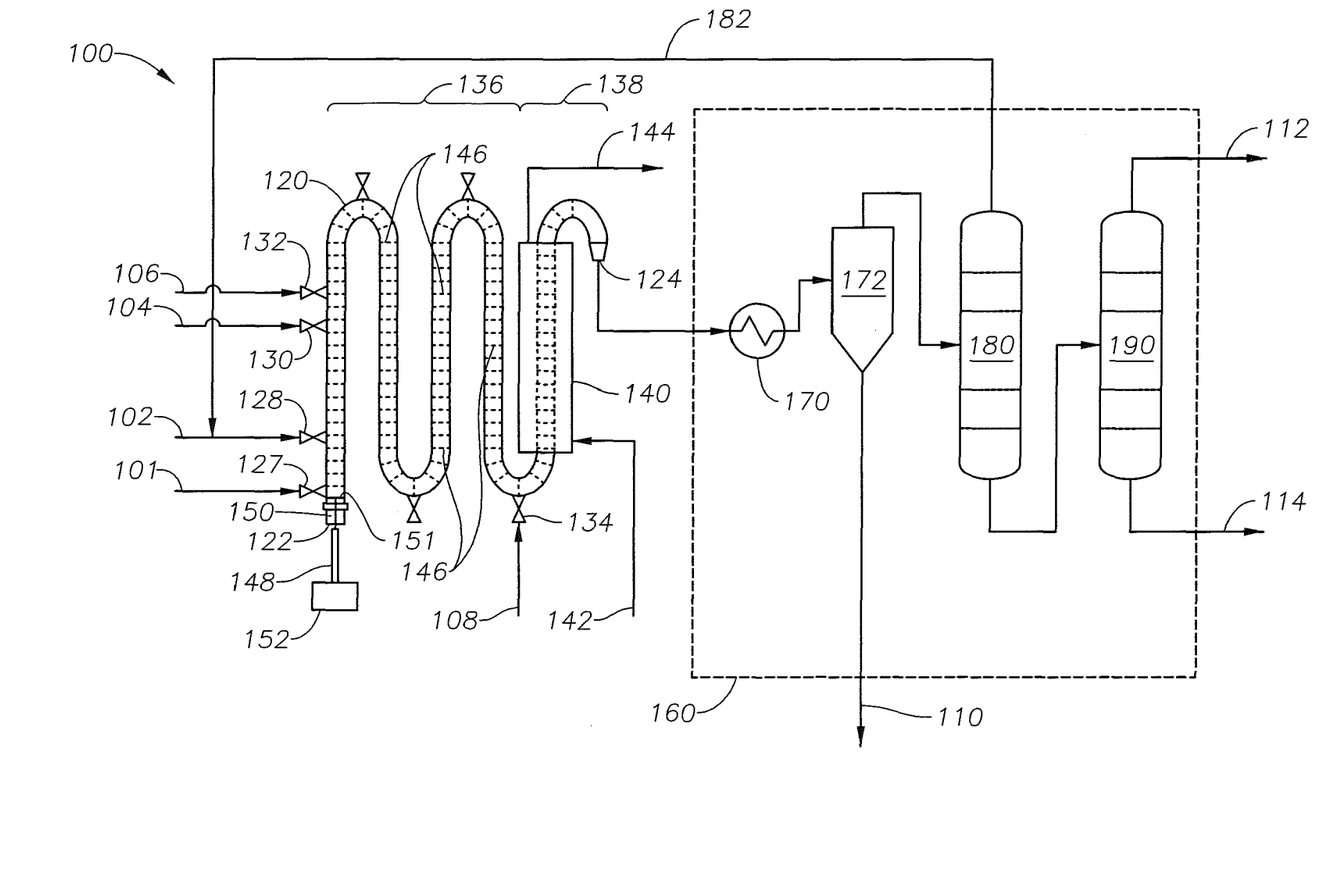
FIG. 1 is a process flow diagram of an embodiment of an ethylene oligomerization system.

FIG. 1

FIG. 1 is a process flow diagram of an embodiment of the ethylene oligomerization system. FIG. 1 and its description facilitate a better understanding of the ethylene oligomerization system and process. In no way should FIG. 1 limit or define the scope of the invention. FIG. 1 is a simple diagram for ease of description.

The ethylene oligomerization process introduces several feeds into ethylene oligomerization system 100, including solution feed 101, ethylene feed 102, catalyst precursor feed 104, co-catalyst feed 106 and catalyst inhibitor 108. Several products pass from ethylene oligomerization system 100, including waste catalyst 110, refined 1-butene product 112 and butenes separator bottoms 114.

Ethylene oligomerization system 100 includes several units that support the conversion of ethylene to 1-butene and the production of refined 1-butene. Internal baffle single pass reactor 120 supports catalytically induced dimerization, which is a form of oligomerization, of ethylene into 1-butene. Solution feed 101, ethylene feed 102, catalyst precursor feed 104, co-catalyst feed 106 and catalyst inhibitor 108 all enter ethylene oligomerization system 100 through internal baffle single pass reactor 120.

In separation system 160 (dashed box), vaporizer 170 couples to internal baffle single pass reactor 120 and is operable to remove solids in the crude product passing from distal end 124 of internal baffle single pass reactor 120. Evaporator 172 couples to vaporizer 170 and is operable to remove any remaining solids in the vaporize effluent, including deactivated oligomerization catalyst from the partially vaporized crude product. Evaporator 172 produces waste catalyst 110 and a catalyst-free crude product. Ethylene recycle column 180 couples to evaporator 172 and is operable to remove unreacted ethylene from the catalyst-free crude product. Ethylene oligomerization system 100 recycles recovered ethylene to the proximal end of internal baffle single pass reactor 120 via ethylene recycle 182. Butene separator 190 couples to ethylene recycle column 180 and is operable to separate 1-butene from the ethylene-free crude product. Butene separator 190 produces refined 1-butene product 112 and butenes separator bottoms 114 as product streams for ethylene oligomerization system 100.

As shown in FIG. 1, the configuration of internal baffle single pass reactor 120 is a serpentine-shaped fluid conduit with proximal end 122 and distal end 124, with distal end 124 coupling to vaporizer 170. Several ports are present along the operable length of internal baffle single pass reactor 120 for selective access to the internal portion of internal baffle single pass reactor 120 from its exterior. Several injection ports 127 provide feed access to the interior of the internal baffle single pass reactor 120, including solution injection port 127, ethylene injection port 128, catalyst precursors injection port 130, co-catalyst precursors injection port 132 and inhibitor injection port 134.

Internal baffle single pass reactor 120 contains a process fluid that acts as the conveyance and heat transfer medium for the exothermic oligomerization reaction. The process fluid flows through internal baffle single pass reactor 120 from proximal end 122 to distal end 124. The process fluid at any point along the length of internal baffle single pass reactor 120 can include a combination of reactants, catalyst precursors, oligomerization catalyst in active and deactivated form and reaction products and by-products. The process fluid contains crude 1-butene product when it passes through distal end 124.

Internal baffle single pass reactor 120 has more than one reaction zone. Oligomerization zone 136, which is a reaction zone, extends along the operable length of internal baffle single pass reactor 120 from ethylene injection port 128 near proximal end 122 to about inhibitor injection port 134. Internal baffle single pass reactor 120 in oligomerization zone 136 supports introduction of ethylene and catalyst components, the creation of 1-butene from the catalytically induced oligomerization reaction of ethylene and the cooling of the process fluid to prevent undesired reactions. Deactivation zone 138, which is another reaction zone, extends along the operable length of internal baffle single pass reactor 120 from about inhibitor injection port 134 to distal end 124. Internal baffle single pass reactor 120 in deactivation zone 138 supports the introduction of catalyst inhibitor and the deactivation of the oligomerization catalyst.

In FIG. 1, temperature control jacket 140 envelopes a portion of internal baffle single pass reactor 120. The configuration of temperature control jacket 140 allows temperature control fluid to provide or extract heat to the enveloped portion of internal baffle single pass reactor 120. Temperature control fluid supply conduit 142 introduces temperature control fluid to and temperature control fluid return conduit 144 extracts spent temperature control fluid from temperature control jacket 140.

Internal baffle single pass reactor 120 has fixed internal baffles 146 along most of its operable length. Internal baffle single pass reactor 120 has fixed internal baffles 146 in oligomerization zone 136 and most of deactivation zone 138. Fixed internal baffles 146 partially define the fluid flow pathway for the process fluid flowing through internal baffle single pass reactor 120. The fluid flow pathway directs the process fluid against the interior surface of internal baffle single pass reactor 120 as well as against fixed internal baffles 146. The flowing process fluid flow disrupts the formation and adhesion of heavy oligomers and polymers to the interior surfaces. Flowing against the interior wall of the internal baffle single pass reactor also facilitates heat transfer. Fixed internal baffles 146 also increase the residence time in internal baffle single pass reactor 120. The fluid flow pathway created by fixed internal baffles 146 and the internal wall of internal baffle single pass reactor 120 is longer to traverse than an analogous single pass reactor without internal baffles.

Process fluid oscillator 148 is near proximal end 122 of internal baffle single pass reactor 120. Process fluid oscillator 148 couples to internal baffle single pass reactor 120 through oscillator seal 150 such that process fluid oscillator 148 moves without exposing external contaminants to the process fluid and without leaking process fluid to the external environment. Process fluid oscillator 148 is in frictional contact with the interior wall of the internal baffle single pass reactor 120 at oscillator head 151. Oscillator head 151 is in contact with the process fluid.

Changing the relative position of process fluid oscillator 148 imparts a position change in the process fluid through oscillator head 151. The position change imparts an unsteadiness in the process fluid as flows through the internal baffle single pass reactor 120. The unsteadiness in the process fluid flow enhances mixing and heat removal. The pushing and pulling on the incompressible process fluid causes the process fluid flow to surge and retreat along the fluid flow pathway. This fluid action improves heat transfer, retards the buildup of polymers and minimizes the effects of any pre-existing "hot spots".

The configuration of oscillator seal 150, the coupling to external motion driver 152 and the contact that oscillator head 151 has with the interior wall of internal baffle single pass reactor 120 operably restricts process fluid oscillator 148 to a limited range of motion. The configuration of process fluid oscillator 148, when operable, moves oscillator head 151 in a back-and-forth linear direction.

The Process Fluid and the Crude Product

"Oligomerization" is the process of converting a monomer or a mixture of monomers into an oligomer. Dimerization, trimerization and tetramerization are forms of oligomerization. In the case of the ethylene oligomerization system and process, the monomer used is ethylene. The products of the system and process include 1-butene, and optionally can also include 1-hexene, 1-octene, 1-decene and other higher-order alpha-olefins.

The internal baffle single pass reactor contains the process fluid, which at any given time along the operable length of the internal baffle single pass reactor includes reaction solution, ethylene, oligomerization products, oligomerization catalyst precursor, co-catalyst, oligomerization catalyst, deactivated oligomerization catalyst and catalyst inhibitors.

Process fluid that passes from the internal baffle single pass reactor is a crude product that contains alpha-olefins, especially 1-butene, as well as unused reactants and reaction by-products. Deactivated oligomerization catalyst, ethylene and refined alpha-olefins, especially 1-butene, are recoverable from the process fluid using the separation system of the ethylene oligomerization system.

The process fluid dissolves introduced ethylene, supports the reaction of the oligomerization catalyst precursor with the co-catalyst, which forms the oligomerization catalyst, supports the oligomerization of ethylene into alpha-olefins, especially 1-butene, in the presence of the oligomerization catalyst and supports the reaction of the oligomerization catalyst with the catalyst inhibitor, which forms the deactivated oligomerization catalyst at the reaction operating conditions.

The process fluid at any point along the operable length of the internal baffle single pass reactor has a total solids and non-organic impurities content less than about 0.1 percent by volume (vol. %) of the process solution. A rise in detectable solids, especially polymerized ethylene and metal oxides, are indicators of fouling and potential development of a hot spot.

An embodiment of the ethylene oligomerization process includes operating such that the temperature of the process fluid is maintained in a range of from about 30° C. to about 110° C., and optionally in a range of from about 40° C. to about 60° C. An embodiment of the ethylene oligomerization process includes operating such that the pressure of the process fluid is maintained in a range of from about 1 bar to about 50 bars gauge, and optionally in a range of from about 15 bars to about 30 bars gauge.

Reaction Solution

The reaction solution forms a significant portion if not the major fraction of the process fluid. The reaction solution is a hydrocarbon-based fluid, typically a liquid or critical fluid at the operating conditions inside the internal baffle single pass reactor.

The reaction solution comprises one or more components. The reaction solution can include aliphatic, cycloaliphatic, mono- and di-olefin, aromatic and alkyl aromatic compounds. An embodiment of the ethylene oligomerization process includes introducing a reaction solution comprising one or more mono-olefins. An embodiment of the ethylene oligomerization process includes introducing a reaction solution comprising 1-butene. An embodiment of the ethylene oligomerization process includes introducing a reaction solution consisting essentially of 1-butene.

In an embodiment of the ethylene oligomerization process, a portion of the refined 1-butene is recycled from the separation system to the internal baffle single pass reactor to supplement the reaction solution. An embodiment of the ethylene oligomerization system includes a configuration in which the internal baffle single pass reactor fluidly couples to the separation system such that the ethylene oligomerization system is operable to pass refined 1-butene to the internal baffle single pass reactor. An embodiment of the ethylene oligomerization process includes operating such that at least a portion of the refined 1-butene product by the ethylene oligomerization system is recycled and is introduced into the process fluid of the internal baffle single pass reactor.

Fresh solution for fluid makeup to the internal baffle single pass reactor is at least 99 volume (vol.) % solution. Non-alkane and alkene impurities are typically less than 100 parts-per-million (ppm).

Ethylene

Introduced fresh ethylene is polymerization-grade and has a purity of at least about 99 volume % (vol. %) ethylene. An embodiment of the ethylene oligomerization process includes introducing ethylene having a purity in a range of from about 99 vol. % to about 99.95 vol. % ethylene. Non-alkane or alkene impurities that can promote or inhibit ethylene oligomerization, oligomerization and polymerization reactions are typically at or below 5 ppm by volume of ethylene.

Recycled ethylene from other parts of the ethylene oligomerization process can improve reactant-based efficiency. An embodiment of the ethylene oligomerization system includes a configuration in which the internal baffle single pass reactor fluidly couples to the separation system such that the ethylene oligomerization system is operable to pass the selectively separated ethylene to the internal baffle single pass reactor. An embodiment of the ethylene oligomerization process includes operating the system such that the ethylene selectively separated by the separation system is introduced into the process fluid of the internal baffle single pass reactor. Recycled ethylene can have a lower purity than fresh ethylene.

Introduction of ethylene can occur as a pressurized gas or a liquid, although preferably in a vaporous state. Pre-heating the introduced ethylene can provide heat to the process fluid and encourage the oligomerization reaction.

Oligomerization Catalyst Precursor, Co-Catalyst and Catalyst Additive

The homogeneous ethylene oligomerization catalyst is an organometallic, active metal reaction product between a transition metal organic catalyst precursor and an alkylating agent co-catalyst. The oligomerization catalyst facilitates the oligomerization of ethylene into alpha-olefins, including 1-butene, 1-hexene, 1-octene, 1-decene and heavier alpha-olefins in the process solution.

The oligomerization catalyst precursor is an organometallic compound or metal complex that includes at least one catalytically active metal from the metals of Groups 3-10 and the Lanthanide series according to the International Union of Pure and Applied Chemistry (IUPAC) Periodic Table of Elements. Although not intending to be bound by theory, it is believed that the catalytically active metal component of the oligomerization catalyst precursor forms a complex with alpha-olefins and part of the process in forming the oligomerization reaction products. An embodiment of the ethylene oligomerization process includes introducing an oligomerization pre-catalyst that includes a transition metal. Useful catalytically active metals include nickel, chromium, titanium and zirconium. The ethylene oligomerization process uses catalyst precursors that are homogeneous, which do not require a supporting medium.

Useful oligomerization catalyst precursors include organometallic compounds of titanium, including tetraalkyl titanates and "titanium alkoxides". In titanium alkoxides, the hydrocarbyl radical portion of each alkoxide includes similar or different alkyl, aryl, cycloalkyl, hetrocyclyl, aralkyl or alkaryl groups. Titanium alkoxide catalyst precursors include tetramethyl titanate, tetraethyl titanate, tetraisopropyl titanate, tetra(n-butyl) titanate and tetra(2-ethylhexyl) titanate.

The alkylating co-catalyst is an organometallic compound that reacts with the oligomerization catalyst precursor in the process fluid to form the oligomerization catalyst. Useful catalytically active metals for co-catalysts include aluminum, magnesium and zinc. An embodiment of the ethylene oligomerization process includes introducing a co-catalyst that is an alkyl of a Group 1-3 or a Group 11-13 metal according to the IUPAC Periodic Table of Elements.

Useful co-catalysts include organometallic compounds of aluminum, which include tri- and dialkyl aluminum compounds. Trialkyl aluminum ("TAL") compounds include triethyl aluminum ("TEAL"), triisobutyl aluminum ("TIBAL"), trihexyl aluminum ("THAL") and tribenzyl aluminum. Dialkyl aluminum compounds include diisobutyl aluminum hydride ("DIBAH"). Other useful aluminum-based co-catalysts include alumininoxanes, examples of which are methylaluminoxane ("MAO") and modified methylaluminoxane ("MMAO").

As part of the process solution in the internal baffle single pass reactor, the oligomerization organometallic catalyst precursor and the co-catalyst react or create a complex with one another such that the active metal oligomerization catalyst forms. Reactions between the oligomerization catalyst precursor and the co-catalyst include swapping organic ligands, which exposes the catalytically active metal to the oligomerization reactants. An embodiment of the ethylene oligomerization process includes introducing the oligomerization catalyst precursor and the co-catalyst separately into the process fluid. The oligomerization catalyst forms in the process solution at the operating conditions for the ethylene oligomerization reaction. An embodiment of the ethylene oligomerization process includes introducing a pre-activated oligomerization catalyst into the process fluid such that the oligomerization catalyst is distributed in the process fluid. In a system outside of the internal baffle single pass reactor, a catalyst mixing system can mix the oligomerization catalyst precursor and the co-catalyst together to form the oligomerization catalyst and then introduce the pre-formed and activated oligomerization catalyst into the process fluid.

Optionally, a catalyst additive is introduced along with the oligomerization catalyst precursor, the co-catalyst or the pre-activated oligomerization catalyst. The catalyst additive can help suppress polymer formation through excessive oligomerization and therefore reduce the rate in which fouling of the internal baffle single pass reactor occurs. An embodiment of the ethylene oligomerization process includes introducing a catalyst additive that includes a Group 14-17 element according to the IUPAC Periodic Table of Elements. Useful catalyst additives include alcohols and amines.

Oligomerization Catalyst Inhibitor

Addition of catalyst inhibitor to the process fluid results in deactivation of the oligomerization catalyst. Deactivating the oligomerization catalyst halts the catalytically supported oligomerization reactions of ethylene into alpha-olefins. The introduction also stops any catalytically supported by-product reactions.

Oxygen, nitrogen and sulfur polar compounds are effective oligomerization catalyst deactivators. Useful oxygen polar compounds include water, carbon dioxide, carbon monoxide, alkyl alcohols, including methanol, and diol aromatics, including tert-butyl catechol and hydroquinone. Useful nitrogen polar compounds include primary and secondary amines, including aniline, methylaniline, decylamine, dibutylamine and cyclohexylamine. Aliphatic, cycloaliphatic and aromatic hydrocarbyl radicals that are part of the catalyst inhibitor can have carbon counts in the range of from 1 carbon to about 22 carbons.

The catalyst inhibitor comprises one or more inhibitors, and can be further diluted in a solvent of the inhibitor for introduction. Introduction as a liquid enhances its dispersion into the process fluid.

Ethylene Oligomerization Products

The primary product of the ethylene oligomerization process is 1-butene, which is an alpha-olefin. Other resultants of the process are deactivated oligomerization catalyst, non alpha-olefins, and assorted alkanes and alkenes. The ethylene oligomerization system is operable to selectively separate 1-butene from the crude product passing from the internal baffle single pass reactor. Optionally, the ethylene oligomerization process produces at least one other refined higher-order alpha-olefin. An embodiment of the ethylene oligomerization system is operable to selectively separate 1-hexene from the crude product. An embodiment of the ethylene oligomerization system is operable to selectively separate 1-octene from the crude product. An embodiment of the ethylene oligomerization system is operable to selectively separate 1-decene from the crude product.

Any solids in the crude product, including polymer and heavy oligomers, deactivated oligomerization catalyst, oligomerization catalyst and rust collect in the waste stream of the separation system. The solid waste can contain liquid materials too heavy to vaporize at the operating conditions of the separations system. Processes outside of the ethylene oligomerization system can recover useful hydrocarbons and valuable metals from the waste product.

Heavy by-products, predominantly olefins and alkanes that have a higher carbon count than the product alpha-olefins recovered by the separation system of the ethylene oligomerization system, pass from the separation system as a bottoms stream. In an embodiment of the ethylene oligomerization process where the highest alpha-olefin recovered is 1-butene, the heavy stream is from a butene separations column and comprises alkanes and alkenes that are C6+. In an embodiment of the ethylene oligomerization process where the highest alpha-olefin recovered is 1-hexene, the heavy stream is from a hexene separations column and comprises alkanes and alkenes that are C8+. In an embodiment of the ethylene oligomerization process where the highest alpha-olefin recovered is 1-octene, the heavy stream is from an octene separations column and comprises alkanes and alkenes that are C10+. In an embodiment of the ethylene oligomerization process where the highest alpha-olefin recovered is 1-decene, the heavy stream is from a decene separations column and comprises alkanes and alkenes that are C12+. Such by-product hydrocarbons, olefins and di-olefins are useful as gasoline blending components.

The ethylene oligomerization process produces a refined 1-butene having a purity of at least about 99 vol. % 1-butene. An embodiment of the ethylene oligomerization process produces a refined 1-butene having a purity in a range of from about 99 to about 99.99 vol. % 1-butene. The major impurity in the refined 1-butene product includes butanes (both normal and iso-) and 2-butene, and the non alpha-olefin isomer of 1-butene. An embodiment of the oligomerization process produces a refined 1-butene that is sufficiently free of 2-butene.

Ethylene Oligomerization System and Process

The ethylene oligomerization system facilitates the selective conversion of ethylene into alpha-olefins. The ethylene oligomerization process produces a refined 1-butene having a minimal amount of 2-butene. Optionally, the ethylene oligomerization process produces refined higher-order alpha-olefins that are sufficiently free of non alpha-olefin isomers.

Internal Baffle Single Pass Reactor

The ethylene oligomerization system includes an internal baffle single pass reactor. The internal baffle single pass reactor is a tube where the internal fluid conduit is operable to support a pressurized, fluid-filled environment for the oligomerization of ethylene. The tube has an interior surface or wall partially enclosing the fixed volume between the first or proximal end and the second or distal end. The operable length of the internal baffle single pass reactor is the length of the tube between the first end and the second end and is much greater than its diameter. The exterior surface or wall along its operable length permits heat to transfer in and out of the reactor.

In the ethylene oligomerization system, the process fluid flows from about the proximal end to about the distal end. The process fluid passes as the crude product to the coupled separations system. The configuration of the tube permits the introduction of process fluid components proximate to the first end, especially reaction solution, which helps drive the process fluid flow through the reactor.

At any given point along the operative length of tube, the internal fluid conduit axis is perpendicular relative to the cross-sectional area of the internal fluid conduit at that point. With no internal additions (that is, no internal baffles), a fluid can traverse the operative length of the tube from about the first end to about the second end. If the flow is non-turbulent (that is, laminar), the fluid flow pathway generally remains aligned relative to the internal fluid conduit axis.

FIG. 1 shows an internal baffle single pass reactor having a serpentine shape; however, this is not required. The internal baffle single pass reactor of the ethylene oligomerization system can take any number of physical configurations based upon the use of connected linear and non-linear fluid conduit segments, including standard pipes.

Process fluid flows through the internal fluid conduit of the internal baffle single pass reactor by the coordinated introduction of process fluid components, especially the solution, about the proximate end and the removal of the crude product about the distal end of the reactor. Flow drivers, including pumps, optionally provide momentum to the process fluid. Auxiliary flow motivation equipment is preferably not located in the oligomerization reaction zone to prevent the formation and aggregation of ethylene-based oligomers and polymers in the housing of the rotating equipment.

The internal baffle single pass reactor has at least one ethylene feed location. The ethylene feed location can introduce fresh, recycled, or a combination of both. An ethylene feed location is typically upstream of or at the beginning of the oligomerization reaction zone. An embodiment of the ethylene oligomerization system includes a configuration in which the internal baffle single pass reactor has more than one oligomerization reaction zone. An embodiment of the ethylene oligomerization process includes introducing ethylene into the process fluid proximate to each oligomerization reaction zone such that the ethylene is distributed into the process fluid in each oligomerization reaction zone.

The internal baffle single pass reactor has at least one catalyst feed location. The catalyst feed location can introduce oligomerization catalyst precursor and co-catalyst either separately or as a combined feed into the process fluid. The ethylene oligomerization process includes introducing the oligomerization catalyst precursor and the co-catalyst separately into the process fluid to permit formation of the oligomerization catalyst in the process fluid. This embodiment permits formation of the oligomerization catalyst away from the catalyst feed location and the interior wall. The catalyst feed location can also introduce pre-activated oligomerization catalyst into the process fluid.

The catalyst feed location is typically upstream of or at the beginning of the oligomerization reaction zone and downstream of an ethylene feed location. The catalyst feed location relative to the ethylene feed location provides adequate distribution time for uniform distribution of the ethylene in the process fluid. Upon introduction into or its formation in the process fluid, the selective ethylene oligomerization reaction occurs nearly instantaneously with ethylene proximate to the activated oligomerization catalyst.

The internal baffle single pass reactor has at least one catalyst inhibitor feed location. Introduction of the catalyst inhibitor occurs through either a singular injection point or multiple injection points in the catalyst deactivation zone. Catalyst inhibitor distribution occurs a suitable distance from the catalyst feed location to permit formation of the oligomerization catalyst and adequate ethylene oligomerization into 1-butene before catalyst deactivation. The catalyst feed location is typically upstream of or at the beginning of the catalyst deactivation zone and after the final oligomerization reaction zone because oligomerization catalyst deactivation is permanent.

The ethylene oligomerization system includes multiple reaction zones. The internal baffle single pass reactor has at least one reaction zone for ethylene oligomerization and one reaction zone for oligomerization catalyst deactivation. An embodiment of the ethylene oligomerization system includes more than one oligomerization reaction zone, each oligomerization reaction zone associated with an ethylene feed location. The position of the ethylene feed location is proximate to the upstream-most portion of the oligomerization reaction zone. An embodiment of the ethylene oligomerization process includes introducing ethylene into the process fluid proximate to each oligomerization reaction zone such that the ethylene is distributed into the process fluid of each oligomerization reaction zone. Multiple oligomerization reaction zones reflect a heightened level of process control over the oligomerization process prior-art loop reactors. In such an embodiment, the system can include a single catalyst feed location associated with the upstream-most oligomerization reaction zone. The position of the single catalyst feed location is proximate to the upstream-most portion of the upstream-most oligomerization reaction zone. In such an embodiment, the system can include a single catalyst inhibitor feed location positioned downstream of the downstream-most oligomerization reaction zone. Each oligomerization and catalyst deactivation zone can have different internal and external processing equipment to support the different reactions, including internal baffle structure and configuration, steadiness of the flow of the process fluid and reaction zone temperature management that reflects the process in each single pass reaction zone.

Internal Baffles

The internal baffle single pass reactor includes a set of stationary internal flow baffles. The internal fluid conduit contains the internal baffles. During the ethylene oligomerization process, stationary baffles are immobile; their position and orientation within the reactor does not change. The process fluid flows against and around the internal baffles as the process fluid traverses the operative length of the reactor along the fluid flow pathway formed by the internal baffles and the reactor. An embodiment of the ethylene oligomerization system includes internal baffles along the entire operating length of the internal baffle single pass reactor. An embodiment of the ethylene oligomerization system includes internal baffles only in the oligomerization reaction zone. Such a configuration supports mixing and flow unsteadiness where oligomerization occurs and less mixing and flow unsteadiness where catalyst deactivation occurs.

The fluid flow pathway through the internal baffle single pass reactor is defined by both the internal tubular wall and the shape of the internal baffles, including flow windows, spacing and orientation relative to the internal fluid conduit axis. The presence of internal baffles creates a fluid flow pathway through the reactor for the process fluid to traverse from the proximal end to the distal end of the reactor. An embodiment of the ethylene oligomerization system includes an internal baffle single pass reactor where the fluid flow pathway is the same length as the operative length of the reactor. A reactor with orifice plates with the flow window centered in each plate can offer such an internally baffled configuration. An embodiment of the ethylene oligomerization system includes an internal baffle single pass reactor where the fluid flow pathway is longer than the operative length of the reactor. The process fluid flow pathway in this configuration is longer than the operative length of the reactor because the internal baffles restrict the flow pathway available to the process fluid, forcing the process fluid to flow along a pathway not in alignment with the internal fluid conduit axis, thereby increasing the distance the process fluid must travel through the reactor.

Internal baffles extend from the interior wall into the internal fluid conduit along a perpendicular plane to the internal fluid conduit axis. Depending on their configuration, the internal baffles can prevent the process fluid from flowing in alignment with the internal fluid conduit axis for the portion of the operative length of the internal baffle single pass reactor in which they are present.

Modification of the process fluid flow direction as the process fluid traverses the length of the internal baffle single pass reactor increases residence time. The increased residence time can improve process control and increase ethylene oligomerization reaction efficiency and selectivity over single-pass systems. The residence time for ethylene oligomerization process is not as long as with conventional loop reactor systems, which as previously described systemically suffer from fouling in the reaction loop system. An embodiment of the ethylene oligomerization process includes operating such that the residence time of the oligomerization catalyst in the reactor is maintained in a range of from about 0.01 to about 2 hours, and optionally about 0.5 hours.

Spacing of the internal baffles relative to one another can have an impact upon the length of the fluid flow pathway and effects on mixing. An embodiment of the ethylene oligomerization system includes where the internal baffle single pass reactor has internal baffles that are spaced equally distant from one another along the operative length of the reactor. The spacing between internal baffles can also be random or varied along the operative length of the reactor. An embodiment of the ethylene oligomerization system includes where the reactor has a first set of internal baffles in a first oligomerization reaction zone having a first spacing distance and a second set of internal baffles in a second oligomerization reaction zone with a second spacing distance. The different reaction zones can be upstream and downstream oligomerization reaction zones or an oligomerization reaction zone and a catalyst deactivation zone.

The internal baffles can have a number of known physical configurations, including rods, perforated plates, mesh screens, orifice plates (centered and off-centered orifice) and segmented plates. The flow window size, its position in the internal fluid, and its configuration relative to other internal baffles are factors in modifying the direction of travel of the process fluid and forming the process fluid flow pathway.

External Motion Driver

The ethylene oligomerization system includes an external motion driver that is operable to induce unsteadiness in the process fluid flow without modifying other operating parameters of the ethylene oligomerization process, including temperature, mass flow rate and pressure. The external motion driver induces unsteadiness by transferring motion into the incompressible process fluid.

The external motion driver couples to an apparatus that is in direct fluid contact with the process fluid. As the process fluid flows through the internal baffle single pass reactor, the external motion driver acts upon the flowing process fluid in a physical manner by conveying motion via the apparatus in contact with the process fluid. The changing motion of the coupled apparatus creates unsteadiness in the process fluid flow. An embodiment of the ethylene oligomerization system includes an external motion driver operable to convey an oscillating motion to the process fluid. An embodiment of the ethylene oligomerization system includes an external motion driver operable to convey a reciprocating motion to the process fluid. An embodiment of the ethylene oligomerization system includes an external motion driver operable to convey a variable motion to the process fluid.

The embodiment of the ethylene oligomerization system shown in FIG. 1 conveys unsteadiness directly into the process fluid through a piston-like apparatus at the proximal end of the internal baffle single pass reactor. Operation of the piston in a back-and-forth manner displaces the process fluid and causes the process fluid flow to surge and regress while generally flowing through the reactor from the proximal end to the distal end. Another embodiment of the ethylene oligomerization system includes a configuration in which the external motion driver is coupled to a diaphragm apparatus in fluid contact with the process fluid. The expansion and contraction of the diaphragm apparatus against the incompressible process fluid directly displaces the expansion and contraction volume of the diaphragm apparatus, transferring the motion into the process fluid flow.

External motion drivers include electrical, electro-mechanical, hydraulic, pneumatic, gas injection, compressed gas, chemical-reaction and any other system or apparatus for imparting or transferring motion into the process fluid such that it induces unsteadiness in the process fluid flow. External motion drivers include reciprocating motors.

Without the application of unsteadiness to the process fluid flow through the external motion driver, the ethylene oligomerization process would otherwise maintain a steady state process fluid flow condition at a given point along the fluid flow pathway. A steady state condition is where fluid properties at any point in the system do not change with time. Although mathematically feasible, most of ordinary skill in the art of petroleum, petrochemical and chemical operations understand that "steady state" operations include some minor, transient process variability.

The application of motion by the external motion driver upon the process fluid changes the steady state flow condition to one that is an unsteady process fluid flow condition during the period of motion inducement. The unsteady condition results in changes to other ethylene oligomerization process conditions, including heat transfer, reaction efficiency and overall productivity of the ethylene oligomerization system in response to the destabilization of the process fluid flow momentum. The period of unsteadiness occurs from the moment of introduction and for a period afterwards with diminishing effects as a function of time. With no additional interaction by the external motion driver and by otherwise maintaining steady operating conditions, achieving a new steady state flow condition is feasible. Repeated or continual application of motion directed into the process fluid by the external motion driver causes a continuous condition of unsteadiness to exist in the process fluid flow.

At any given moment during the ethylene oligomerization process, the relative motion introduction alters the momentum (for example, accelerated, retarded) of the process fluid flowing from the proximal end to the distal end. The inducement of the unsteady condition in the process fluid flow does not affect the total volumetric or mass flow through the internal baffle single pass reactor. For the ethylene oligomerization process, introduction of process fluid components and the passing of crude product typically remain constant whether there is inducement of unsteadiness or not.

Transient formation and dissipation of fluid eddies and counter-flows in the process fluid flow occur during unsteady flow. The eddies and counter-flows in the process fluid occur at the sharp edges of the flow windows of the internal baffles. Although resembling the random directional flow associated with turbulence, unsteady flow also occurs in low Reynolds number flow regimes. The unsteady process fluid flow encourages mixing, reactions and heat transfer by causing a non-majority portion of the process fluid flowing through the internal baffle single pass reactor at any given time for a transient period to flow in an unpredictable and non-steady state-like manner.

The internal baffles during the inducement of unsteadiness can cause the process fluid to contact the interior wall at near-perpendicular angles. Fluid flowing directly against a surface at a steep angle, which includes perpendicular to the interior wall, does not support the adhesion of solids to the interior wall surface; rather, the flow friction against the wall surface tends to remove and prevent solids build-up. The unsteady process fluid flowing against the interior wall also supports heat transfer from the process fluid to a temperature regulation system along the exterior of the internal baffle single pass reactor. Unsteadiness in the process fluid flow continues until flow momentum along the fluid flow pathway overcomes the induced unsteadiness.

Separation System and Recycles

The ethylene oligomerization system includes units and systems for separating alpha-olefins from the crude product to produce the refined 1-butene and optionally other higher-order alpha-olefins and to minimize isomerization of the alpha-olefins into non-alpha olefins.

The ethylene oligomerization process selectively separates the deactivated catalyst from the crude product to produce a catalyst-free crude product. The ethylene oligomerization system is operable to extract a catalyst-free crude product from the crude product passed from the internal baffle single pass reactor. An example of a unit or system that is useful for extracting catalyst-free crude product from the crude product includes a vaporizer or an evaporator. A useful vaporizer is operable to introduce heat into the crude product such that the lighter portions of the crude product form a vapor, leaving a non-vapor remnant. A useful evaporator is operable to separate portions of the crude product that can achieve a vapor state from the remaining high-temperature boiling products and solids. Useful evaporators include thin-film evaporators. The remnant solids include deactivated oligomerization catalyst, heavy oligomers and by-product polymers.

The ethylene oligomerization process selectively separates ethylene from the catalyst-free crude product such that both the ethylene-free crude product and a recyclable ethylene form. The ethylene oligomerization system is operable to separate unreacted ethylene from the catalyst-free crude product and form an ethylene-free crude product and ethylene suitable for recycling. An example of a useful unit includes an ethylene separations column.

The recyclable ethylene is useful for reintroduction into the internal baffle single pass reactor to improve reactant process efficiency. An embodiment of the ethylene oligomerization process includes operating the system such that the ethylene recovered from the crude product is passed from the separation system and introduced into the internal baffle single pass reactor. An embodiment of the ethylene oligomerization system couples the internal baffle single pass reactor to the separation system such that the system is operable to pass recovered ethylene from the separation system to the internal baffle single pass reactor.

The ethylene oligomerization process selectively separates 1-butene from the catalyst-free crude product such that a refined 1-butene forms. The ethylene oligomerization system is operable to separate 1-butene from the ethylene-free crude product and form refined 1-butene. The refined 1-butene is useful as a product of the system and process. An example of a useful unit includes a 1-butene extraction column.

The refined 1-butene is also useful for recycling and reintroduction into the internal baffle single pass reactor as reaction solution. An embodiment of the ethylene oligomerization process includes operating the system such that refined 1-butene is passed from the separation system and introduced into the internal baffle single pass reactor. An embodiment of the ethylene oligomerization system couples the internal baffle single pass reactor to the separation system such that the system is operable to pass a portion of the refined 1-butene to the internal baffle single pass reactor. The residual crude product contains alkane and alkene C6+ compounds.

Optionally, the ethylene oligomerization system is operable to separate and refine and higher-order alpha-olefins from the crude product downstream from the portion of the system that recovers and refines 1-butene. An embodiment of the ethylene oligomerization process selectively separates 1-hexene from the crude product such that a refined 1-hexene forms. An embodiment of the ethylene oligomerization system is operable to separate 1-hexene from the crude product and form the refined 1-hexene. An embodiment of the ethylene oligomerization process selectively separates 1-octene from the crude product such that a refined 1-octene forms. An embodiment of the ethylene oligomerization process selectively separates 1-decene from the crude product such that a refined 1-decene forms.

What is claimed is:

1. An ethylene oligomerization process for creating a refined 1-butene product from ethylene using an ethylene oligomerization system, the ethylene oligomerization process comprising the steps of:
    introducing a reaction solution into a process fluid contained in an internal fluid conduit of an internal baffle single pass reactor at about a proximal end of the reactor such that the process fluid traverses an operative length of the reactor by flowing along a process fluid flow pathway;
    introducing ethylene, an oligomerization pre-catalyst and a co-catalyst separately into the process fluid proximate to an oligomerization reaction zone such that the ethylene, the oligomerization pre-catalyst and the co-catalyst are distributed in the process fluid;
    introducing a catalyst inhibitor into the process fluid in a catalyst deactivation zone disposed in the internal baffle single pass reactor by way of a catalyst inhibitor injection port in fluid communication with the internal fluid conduit to terminate all oligomerization and side-reactions, the catalyst deactivation zone extending along the operable length of the internal baffle single pass reactor from about the catalyst inhibitor injection port to a distal end of the internal baffle single pass reactor, such that the catalyst inhibitor is distributed in the process fluid;
    passing unused catalyst inhibitor from the distal end of the internal baffle single pass reactor to avoid buildup of unused catalyst inhibitor in the internal baffle single pass reactor; and
    operating the ethylene oligomerization system such that
        an oligomerization catalyst forms in the process fluid from the reaction of the oligomerization pre-catalyst and the co-catalyst in the oligomerization reaction zone,
        1-butene forms in the process fluid from an oligomerization reaction of ethylene in the presence of the oligomerization catalyst in the oligomerization reaction zone,
        a deactivated oligomerization catalyst forms in the process fluid from the reaction of the oligomerization catalyst and the catalyst inhibitor in the catalyst deactivation zone,
        an external motion driver having a process fluid oscillator moves an oscillator head in a back-and-forth linear direction to induce unsteadiness in the flow of the process fluid,
        a crude product passes into a separation system, the crude product comprising the 1-butene, unreacted ethylene from the ethylene oligomerization, and the deactivated oligomerization catalyst, and
        the separation system removes the deactivated oligomerization catalyst, the unreacted ethylene and the 1-butene separately from the crude product such that a refined 1-butene product is produced;
    where the ethylene oligomerization system comprises the internal baffle single pass reactor, the separation system and the external motion driver, where the internal baffle single pass reactor has the oligomerization reaction zone and the catalyst deactivation zone and where the catalyst deactivation zone is positioned downstream of the oligomerization reaction zone.

2. The process of claim 1 where the reaction solution comprises 1-butene.

3. The process of claim 2 where the reaction solution consists essentially of 1-butene.

4. The process of claim 1 where the oligomerization pre-catalyst includes a transition metal and the co-catalyst is an alkyl of a Group 1-3 or a Group 11-13 metal according to the IUPAC Periodic Table of Elements.

5. The process of claim 1 further comprising the step of introducing a catalyst additive that includes a Group 14-17 element according to the IUPAC Periodic Table of Elements into the process fluid proximate to the oligomerization reaction zone such that the catalyst additive is distributed in the process fluid.

6. The process of claim 1 further comprising the step of operating the ethylene oligomerization system such that the temperature of the process fluid within the internal baffle single pass reactor is maintained in a range of from about 30° C. to about 110° C.

7. The process of claim 1 further comprising the step of operating the ethylene oligomerization system such that the pressure of the process fluid within the internal baffle single pass reactor is maintained in a range of from about 1 bar to about 50 bars gauge.

8. The process of claim 1 further comprising the step of operating the ethylene oligomerization system such that the residence time of the oligomerization catalyst in the internal baffle single pass reactor is maintained in a range of from about 0.01 to about 2 hours.

9. The process of claim 1 further comprising the steps of operating the ethylene oligomerization system such that 1-hexene forms in the process fluid from the oligomerization reaction of ethylene in the presence of the oligomerization catalyst in the oligomerization reaction zone, wherein the crude product further comprises the 1-hexene and such that the separation system separates 1-hexene from the crude product such that a refined 1-hexene product is produced.

10. The process of claim 1 further comprising the steps of operating the ethylene oligomerization system such that 1-octene forms in the process fluid from the oligomerization reaction of ethylene in the presence of the oligomerization catalyst in the oligomerization reaction zone, wherein the crude product further comprises the 1-octene and such that the separation system separates 1-octene from the crude product such that a refined 1-octene product is produced.

11. The process of claim 1 further comprising the steps of operating the ethylene oligomerization system such that 1-decene forms in the process fluid from the oligomerization reaction of ethylene in the presence of the oligomerization catalyst in the oligomerization reaction zone, wherein the crude product further comprises the 1-decene and such that the separation system separates 1-decene from the crude product such that a refined 1-decene product is produced.

12. The process of claim 1 further comprising the step of operating the ethylene oligomerization system such that at least a portion of the refined 1-butene product is recycled from the separation system and is introduced into the process fluid of the internal baffle single pass reactor.

13. The process of claim 1 further comprising the step of operating the ethylene oligomerization system such that the unreacted ethylene that is separated from the crude product is recycled from the separation system and is introduced into the process fluid of the internal baffle single pass reactor.

14. The process of claim 1 where the ethylene oligomerization system has more than one ethylene oligomerization reaction zone, the process further comprising the step of introducing ethylene into the process fluid proximate to each oligomerization reaction zone such that the ethylene is distributed into the process fluid in each oligomerization reaction zone.

* * * * *